(12) United States Patent
Clausen et al.

(10) Patent No.: US 10,021,496 B2
(45) Date of Patent: Jul. 10, 2018

(54) METHOD AND SYSTEM FOR CREATING NON-OCCLUDING EARPIECES

(75) Inventors: Tais Clausen, Copenhagen (DK); Rune Fisker, Virum (DK); Nikolaj Deichmann, Copenhagen (DK); David Fischer, Stenlose (DK)

(73) Assignee: 3SHAPE A/S, Copenhagen K (DK)

( * ) Notice: Subject to any disclaimer, the term of this patent is extended or adjusted under 35 U.S.C. 154(b) by 1916 days.

(21) Appl. No.: 12/278,285

(22) PCT Filed: Feb. 9, 2007

(86) PCT No.: PCT/DK2007/000066
§ 371 (c)(1),
(2), (4) Date: Sep. 25, 2009

(87) PCT Pub. No.: WO2007/090407
PCT Pub. Date: Aug. 16, 2007

(65) Prior Publication Data
US 2010/0017006 A1    Jan. 21, 2010

(30) Foreign Application Priority Data
Feb. 10, 2006    (DK) .................................. 2006 00196

(51) Int. Cl.
*H04R 25/00* (2006.01)
*B29C 33/38* (2006.01)
(Continued)

(52) U.S. Cl.
CPC .......... *H04R 25/658* (2013.01); *A61F 11/008* (2013.01); *B29C 33/3835* (2013.01);
(Continued)

(58) Field of Classification Search
CPC ..... A61F 11/08; H04R 1/1016; H04R 1/1058; H04R 1/26; H04R 25/48; H04R 25/60;
(Continued)

(56) References Cited

U.S. PATENT DOCUMENTS 5,487,012 A    1/1996 Topholm et al.
6,937,348 B2 *  8/2005 Geng ................. G01B 11/2509
                                                356/602
(Continued)

FOREIGN PATENT DOCUMENTS

EP            0516808 A1    12/1992
WO        WO-0230157         4/2002
(Continued)

OTHER PUBLICATIONS

Hearing-aids, Southwestern Hearing Centers, Jul. 15, 2013, 4 pages.*

*Primary Examiner* — Crystal J Barnes-Bullock
(74) *Attorney, Agent, or Firm* — Buchanan Ingersoll & Rooney PC (57) ABSTRACT

The present invention provides a method for computer-controlled creation of non-occluding earpieces with tube bore. The non-occluding earpieces are created based on a three-dimensional computer model of at least part of the outer ear and at least part of the auditory canal. The said model is created by a laser scanner, in the ear scanner or by other means. The said three-dimensional computer model is virtually modified to create the non-occluding earpieces and the tube bore. Finally the physical non-occluding earpieces are manufactured using rapid prototyping equipment.

18 Claims, 5 Drawing Sheets

(51) Int. Cl.
*A61F 11/00* (2006.01)
*B33Y 50/00* (2015.01)
*G06F 17/50* (2006.01)
*H04R 1/10* (2006.01)
*B33Y 80/00* (2015.01)

(52) U.S. Cl.
CPC .......... *B29C 33/3842* (2013.01); *B33Y 50/00* (2014.12); *G06F 17/50* (2013.01); *H04R 1/1016* (2013.01); *H04R 25/70* (2013.01); *B33Y 80/00* (2014.12); *H04R 25/652* (2013.01); *H04R 2225/77* (2013.01); *H04R 2460/09* (2013.01); *H04R 2460/11* (2013.01)

(58) Field of Classification Search
CPC ............... H04R 25/652; H04R 25/658; H04R 2460/11; H04R 2460/17; H04R 2225/77; H04R 25/552; B33Y 50/00; B33Y 70/00; B33Y 80/00; B29C 33/3835; B29C 33/3842; B29C 33/448; B29C 64/00; B29C 67/0051; G06F 17/50
See application file for complete search history.

(56) References Cited

U.S. PATENT DOCUMENTS

| | | | | |
|---|---|---|---|---|
| 7,233,676 B2* | 6/2007 | Bayer | ............. | 381/328 |
| 7,412,068 B2* | 8/2008 | Bayer | ............. | 381/328 |
| 7,590,255 B2* | 9/2009 | Nielsen | ............. | H04R 25/656 381/328 |
| 7,844,065 B2* | 11/2010 | von Dombrowski | .. | H04R 25/48 381/328 |
| 8,032,337 B2* | 10/2011 | Deichmann et al. | ............. | 703/1 |
| 8,190,280 B2* | 5/2012 | Bindner | ............. | G05B 19/4097 345/420 |
| 8,422,710 B2* | 4/2013 | Niederdrnk | ......... | H01Q 1/273 381/328 |
| 8,437,489 B2* | 5/2013 | von Dombrowski | .. | H04R 25/48 381/328 |
| 2004/0107080 A1* | 6/2004 | Deichmann | ............. | A61F 11/08 703/6 |
| 2004/0133066 A1* | 7/2004 | Mann | ............. | H04R 25/554 600/25 |
| 2004/0165741 A1* | 8/2004 | Fang | ............. | H04R 25/658 381/322 |
| 2006/0078141 A1* | 4/2006 | Jessen | ............. | H04R 25/402 381/313 |
| 2006/0159298 A1* | 7/2006 | von Dombrowski | .. | H04R 25/48 381/330 |
| 2012/0232857 A1* | 9/2012 | Fisker | ............. | B29C 33/3835 703/1 |

FOREIGN PATENT DOCUMENTS

| WO | WO-02071794 | 9/2002 |
|---|---|---|
| WO | WO-2004/057916 | 7/2004 |

* cited by examiner

METHOD AND SYSTEM FOR CREATING NON-OCCLUDING EARPIECES

FIELD OF INVENTION

The present invention relates to a method for computer-controlled modelling of customized earpieces that can be used as part of communication devices, and more particularly, the invention relates to a method for creating non-occluding earpieces with tube bore.

BACKGROUND OF INVENTION

Non-occluding ear moulds are the new trend in the market for behind-the-ear (BTE) hearing aids and personal communication devices. Instead of filling the auditory canal of the user's ear, an alternative shape is created that allows air to flow freely in and out of the inner ear. Many users of ear molds complain that an occluded ear mold causes discomfort when chewing or that they feel secluded from their surroundings. Also non-occlusion improves wearability as there is nothing to irritate the canal of the ear.

Existing methods to model and manufacture customized non-occluding earpieces are manual, time consuming, and tedious. This form of manual work also introduces a great deal of uncertainty of the finished product. The process typically begins with an impression of the user's ear canal and helix area. Through computer-assisted methods an occluding ear mould is produced which is then grinded to a non-occluded type by hand. This method is a waste of materials, the result often vary between each produced mould and the risk of grinding too close to the inner bore is high—causing the whole work process to be iterated all over.

SUMMARY

The present invention relates to a method for creating non-occluding earpieces with or without a tube bore. The produced earpiece models have a non-occluding canal area, wherein the canal area is the part of the earpiece positioned in the entrance to the auditory canal. These earpieces could include housings for hearing aids, wireless or connected communication devices (headphones, mobile phones, behind-the-ear (BTE) hearing aids, personal agents), loud speakers, tinnitus masking devices, devices recording vibrations in the skull and transforming these into audio signals, voice recognition devices, Man Machine Interface (MMI) products or related to wireless Internet applications. All of these devices may be worn in the user's meatus and/or auditory canal.

Thus, in one aspect the present invention relates to a method for producing a non-occluding earpiece model comprising     obtaining a three-dimensional occlusive computer model of at least a part of the outer ear and at least a part of the auditory canal, said model comprising an outer ear part and a canal part,     selecting an area of interest of the three-dimensional model, thereby obtaining an earpiece computer model having a non-occluding canal area.

In the present context the term "occlusive" means that an earpiece based on the occlusive model would be occluding at least a part of the auditory canal.

In another aspect the present invention relates to a computer program capable of executing program code conducting the method for creating non-occluding earpieces.

In a further aspect the invention relates to a system and a method for producing a non-occluding earpiece, wherein the system comprises means for conducting the method for producing a non-occluding earpiece model, as well as means for producing a non-occluding earpiece from said non-occluding earpiece model.

DETAILED DESCRIPTION OF THE INVENTION

All three-dimensional models of the present invention may be obtained by scanning an impression or by direct scanning of the outer ear and the auditory canal, wherein the scanning may be performed using any suitable method, such as laser scanning, white light, in the ear scanning, ultrasound scanning, MR scanning or CT scanning.

In the following, embodiments of the invention are described in relation to the drawings by following a series of steps conducted.

Step 1: Cut the Canal

Figure 4:
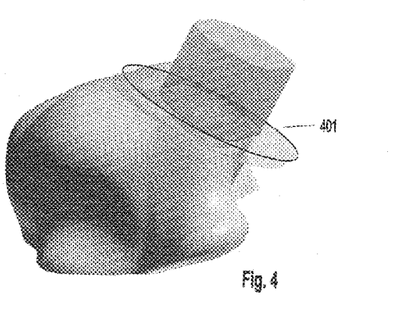
FIG. 4 shows the model of FIG. 1 wherein a cutting surface is provided.
Figure 5:
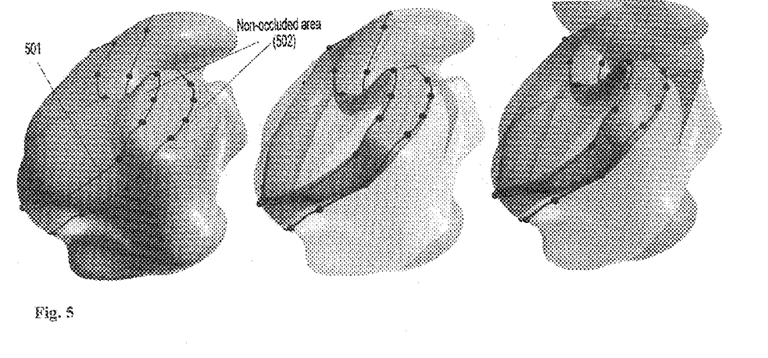
FIG. 5 shows various steps in selecting an area of interest.

In one embodiment the canal (301) of the impression is cut with a cutting surface (401) creating a trimmed surface (402). Said cutting surface may be a simple plane, a bicubic surface, or another parametric surface. The edges of the cut may be pre or post processed to avoid sharp bends. Otherwise the sharp edges may cause irritation to the user of the ear mould. The cut determines the depth of the ear mould into the canal, and may be cut at any suitable distance from the canal area.

Step 2: Create Non-Occluding Shape

Figure 1:
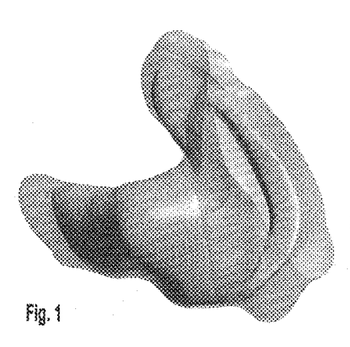
FIG. 1 shows arrangement of a conventional occluding earpiece in the ear.
Figure 2:
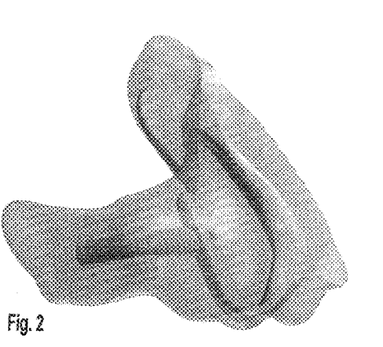
FIG. 2 shows arrangement of a non-occluding earpiece with a tube bore in the ear.
Figure 3:
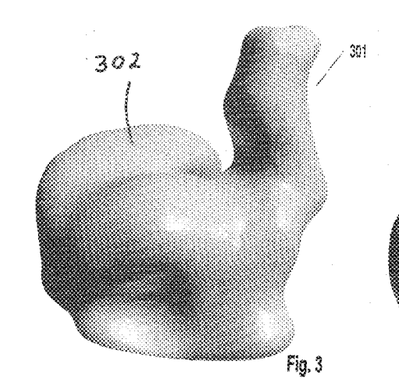
FIG. 3 shows an occlusive model of at least a part of the outer ear and at least a part of the auditory canal.
Figure 6:
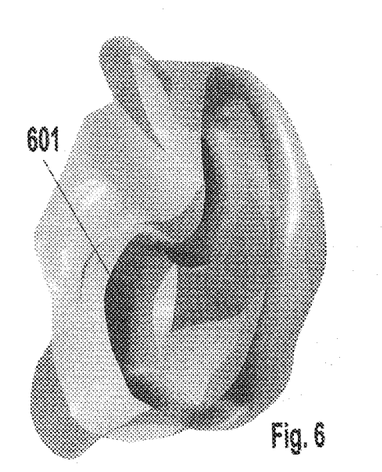
FIG. 6 shows an example of a non-occluding shape.
Figure 7:
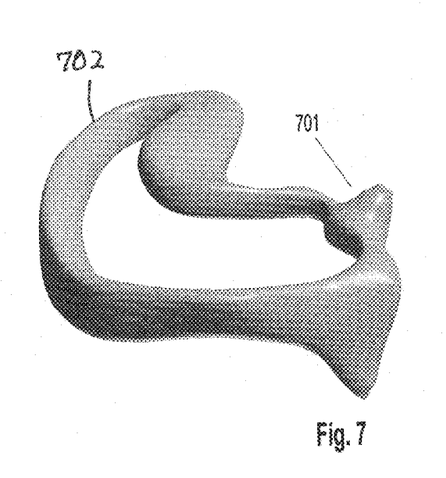
FIG. 7 shows a shape from a CAD model merged with the earpiece model.

Define the shape of the ear mould by selecting the area of interest of the three-dimensional model resulting in an earpiece model having a non-occluding portion that fits in the conchal bowl of the outer ear area. FIG. 3 illustrates the portion (302) that is defined by the conchal bowl adjacent the portion (301) that is defined by the auditory canal. It could be achieved by painting on the impression or using splines (501) to define what needs to be cut away. Placing splines on the newly created surface from step 1, results in a non-occluding ear mould when constructing the shape (502). An example of a non-occluding shape can be seen on FIG. 6. An example of the outer ear portion including a ring of material 702 for contacting the conchal bowl of the ear can be seen in FIG. 7. When used with BTEs, the ear mould should fixate a tube coming from the hearing aid device placed behind the ear. The fixation can be achieved by gluing the tube to the ear mould, drilling a hole in the ear mould, or simply leaving a hole in the area of interest when constructing it.

These methods provide the crudest implementations of non-occluding ear moulds but often these are not enough to satisfy the needs of the user. To improve perceived sound quality, the sound should be shielded as far as possible into the canal—still without blocking the free passage of air. This could be achieved by extending the tube into the canal (301). It is preferred that such a tube is a rigid body, whereby it can be prevented by determining the shape, that the tube cannot touch the sides of the canal (301). As a rigid body extension needs to be fixed to the ear mould to fulfil its purpose, it may be seen as a part of the ear mould. Such an extension will henceforth be referred to as a tube bore.

Step 3a: Create Tube Bore from a Fixed Shape

To direct the sound towards the ear drum at the end of the canal (301) a tube model can be applied to the canal area of the ear mould (601) creating a tube bore in the non-occluding earpiece model. A simple way to produce such a tube is to apply a fixed shape, e.g. a CAD model, to the canal area (601). The shape will be merged with the ear mould through a Boolean OR operation on the two solids. A shape derived from a CAD model (701) can be seen merged with the ear mould on FIG. 7. Subsequently, another fixed shape may be Boolean subtracted from the ear mould to produce the bore through which the sound will pass. Alternatively, the tube from the BTE may be glued to the canal extension of the ear mould or the fixed shape (701) may include fixation points.

Step 3b: Create Tube Bore from Control Path

Using a fixed shape for the tube bore can be disadvantageous as no ears are similar. A fixed shape may collide with the ear of the user and thus alleviate the benefits of a non-occluding ear mould. Instead the tube bore can be generated from the canal part of the occlusive model. In practice the tube bore can be created by defining a control path through the canal (301) from which the tube bore shape can be generated.

Figure 8:
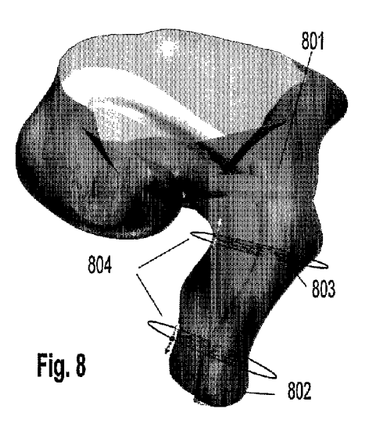
FIG. 8 shows construction of control path in the canal part of the occlusive model.

The control path may be a curve such as a spline with control points that enables manipulation. In the preferred embodiment, a spline is used with an end point (801) at the canal area (601) and a point at the tip of the canal (802) and at least one control point in between (803). The control points (801, 802, 803) may be applied manually, using template based placement, morphologic, or topologic criteria based placements. One possibility to manipulate the at least one control point (803) is by using a plane (804) to which the control point (803) is restrained. The control point (803) can be moved in the plane (804) and the plane (804) itself can be tilted and slit up and down along its normal. Thus, the control point (803) can be positioned at any 3D coordinate. Using a plane (804) also enables the user to manipulate the length of the tube bore and the angle at which the tube bore is cut off by letting the plane of the at least one planes closest to the tip of the canal (301) be the stop point for the generated shape.

Constructing the shape can be done by producing a cylinder around the control path or by defining a 2D template shape that is extruded along the control path. It should be understood that the cylinder is simply a circle template extruded along the control path. Several different templates could be used for the generation of the shape. Either by interpolating between two templates associated with the end points (801, 802) or associating templates with each control point (803).

Figure 9:
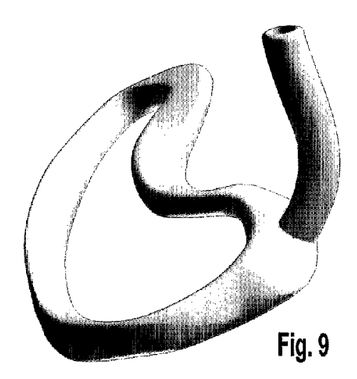
FIG. 9 shows a non-occluding earpiece with a tube bore.

The shape generated from the control path defined by the spline can be used for merging with the non-occluded part (601) similar to the process described in 3a as either the additive or subtractive shape described in step 3a. Producing the other shape, additive or subtractive respectively, can be done as an offset from the first shape-outwards to produce an additive shape and inwards to produce a subtractive shape. Alternatively, the tube from the BTE may be glued to the produced shape. An example of a non-occluding ear mould with a tube bore constructed using a control path can be seen on FIG. 9.

Step 4: Optional Components at the Tube Bore

Figure 10:
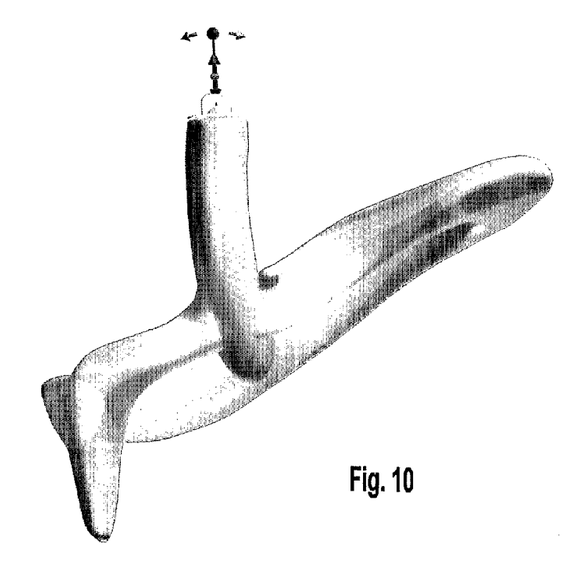
FIG. 10 shows production of a tube bore using a combination of techniques.

In order to design more advanced ear moulds a fixed shape could be applied to the non-occluding earpiece, such as a fixed shape for fixation means for fixing a tube from a hearing aid device. The fixed shape or optional component is a post application of at least one fixed shape to the ear mould by a Boolean operation. Such shapes could also produce hooks, interfaces, wax guards, transmitters, etc. The optional component will initially be placed at either of the control points (801,802,803) and can then be manipulated in relation to this point. This manipulation includes tilting, rotation, panning and relocation. An example of such manipulation can be seen on FIG. 10.

Step 5: Using Subtraction for Creation of Tube Bore

In a different embodiment of the invention the tube bore is produced by exchanging step 1 with a Boolean subtractive operation in which the canal (301) is reduced to the tube bore by a shape that can be defined as in step 3 or 4, but is instead composed of the complementary shape to the one generated in those steps. Subtracting this from the impression produces the same result as achieved by step 3 or 4.

Composite Construction Possibilities

Figure 11:
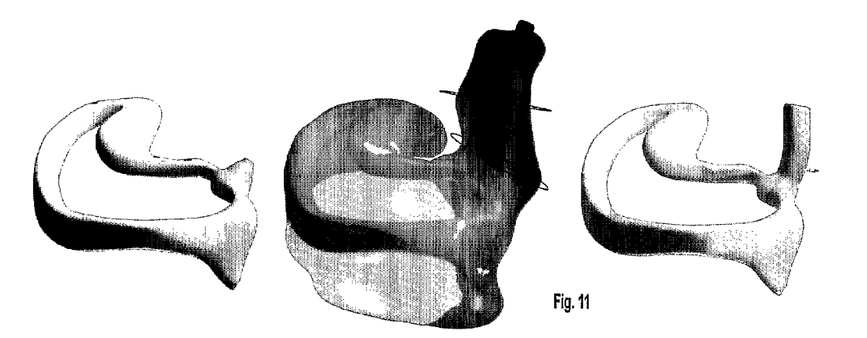
FIG. 11 shows manipulation of an optional component.

Producing a non-occluding ear mould is not restricted to using either step 3a, 3b, or 5. They can be combined to produce ear moulds with specific features. E.g. a fixed shape could be applied first and afterwards a shape derived from a control path could be applied. In FIG. 11, this approach is depicted. Also, using the control points (801,802,803) to signify sections of the canal (301) and either step or a combination of them could be applied separately to each section.

Furthermore according to the present invention, there is provided a method for modelling the complete 3D earpiece with all its surfaces. The fact that the complete earpiece can be modelled also makes it possible to rapid prototype the whole piece in one operation.

Figure 12:
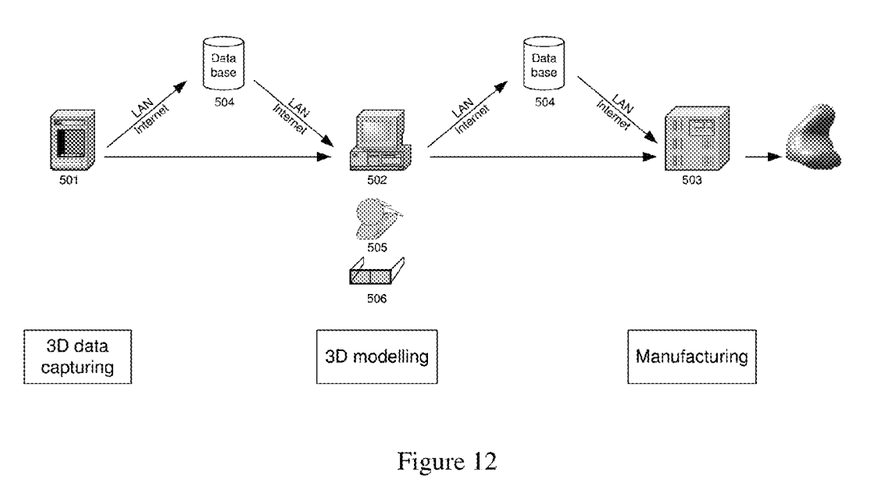
FIG. 12 shows an overview of the process and a computer and a rapid prototyping machine.

Thus, the present invention also relates to a system comprising a computer and a rapid prototype machine. In a preferred embodiment the system further comprises a three-dimensional scanning device for providing the three-dimensional occluding earpiece model.

Thereby the physical version of the final non-occluding three-dimensional model may be produced using a rapid prototyping set-up such as Milling, stereo lithography/SLA, solid ground curing, selective laser sintering, direct shell production casting, 3D-printing, topographic shell fabrication, fused deposition modelling, inkjet modelling, laminated object manufacturing, nano-printing or any other system that produces real models from 3D computer models.

The content of WO 02/071794 and EP 0 516 808 describes methods and systems for obtaining a three-dimensional model of an earpiece as well as production of the earpiece and the methods and systems described in WO 02/071794 and EP 0 516 808 may be used in the present invention. Therefore the description of WO 02/071794 and EP 0 516 808 is hereby incorporated by reference.

The invention claimed is:

1. A method for producing a computer-generated non-occluding earpiece model, the method comprising:
   obtaining a scan of a conchal bowl in an outer ear and an auditory canal adjacent to the conchal bowl or of an impression of the conchal bowl in the outer ear and the auditory canal;
   creating a three-dimensional occlusive computer model of at least a part of the conchal bowl and at least a part of the auditory canal from the scan, said three-dimensional occlusive computer model substantially conforming to a shape of the part of the conchal bowl or the part of the auditory canal or both, said model further including a feature to enable cooperation with electronics located outside of the ear to aid hearing without occluding the conchal bowl and the auditory canal;
   selecting an area of interest of the three-dimensional model resulting in an earpiece model having a non-occluding conchal bowl part and a non-occluding auditory canal part, the area of interest including a portion of the conchal bowl part and a portion of the auditory canal part of the three-dimensional model, the area of interest of the three-dimensional model being selected so as to create an earpiece model that is substantially open in the conchal bowl portion and in the auditory canal part to ensure that the earpiece model is non-occlusive; and
   removing the portion of the three-dimensional occlusive computer model that does not include the area of interest, thereby obtaining an earpiece computer model for a hearing aid having a non-occluding conchal bowl part, a non-occluding canal area part, and a feature to enable cooperation with electronics located outside of the ear to aid hearing without occluding the conchal bowl and the auditory canal.

2. The method according to claim 1, wherein at least a part of the canal part is cut to obtain a trimmed surface before selecting the area of interest.

3. The method according to claim 2, wherein the trimmed surface corresponds to the canal area.

4. The method according to claim 1, wherein the method further comprises creating a tube bore in the non-occluding earpiece model.

5. The method according to claim 4, wherein the tube bore is provided by applying a model of a tube to the non-occluding canal area.

6. The method according to claim 5, wherein a bore in the tube bore is provided by subtracting a fixed shape from the model of the tube.

7. The method according to claim 4, wherein the tube bore is created by defining a control path through the canal part of the occlusive model, and generating a tube bore shape from said control path.

8. The method according to claim 4, wherein the tube bore is generated by boolean addition and/or subtraction from the canal part of the occlusive model to obtain the tube bore.

9. The method according to claim 4, wherein the tube bore is generated from the canal part of the occlusive model.

10. The method according to claim 4, wherein the tube bore is generated by applying a model of a tube to the non-occluding canal area and subsequently modifying the shape of the tube model by defining a control path through the canal part of the occlusive model, and generating a tube bore shape from said control path.

11. The method according to claim 1, said method further comprising defining a fixed shape to be applied to the non-occluding earpiece model for fixing a tube from a hearing aid device.

12. The method according to claim 1, wherein the step of selecting an area of interest of the three-dimensional model, also results in an earpiece model having a non-occluding conchal bowl part.

13. A method for producing a non-occluding earpiece for a behind-the-ear hearing aid, said method comprising providing a prototyping machine, and providing a non-occluding earpiece model as produced by the method of claim 1, and producing on said prototyping machine a non-occluding earpiece from said non-occluding earpiece model.

14. The method according to claim 1, wherein the outer ear portion includes a ring of material for contacting the conchal bowl of the ear.

15. The method according to claim 1, wherein the feature enables connection with a behind-the-ear hearing aid.

16. A nontransitory computer readable medium, said nontransitory computer readable medium having a computer program stored thereon, said program for producing a non-occluding earpiece model comprising program code for conducting the steps of:
   obtaining a scan of a conchal bowl in an outer ear and an auditory canal adjacent to the conchal bowl or of an impression of the conchal bowl in the outer ear and the auditory canal;
   creating a three-dimensional occlusive computer model of at least a part of the conchal bowl and at least a part of the auditory canal from the scan, said three-dimensional occlusive computer model substantially conforming to a shape of the part of the conchal bowl or the part of the auditory canal or both, said model further including a feature to enable cooperation with electronics located outside of the ear to aid hearing without occluding the conchal bowl and the auditory canal;
   selecting an area of interest of the three-dimensional model resulting in an earpiece model having a non-occluding conchal bowl part and a non-occluding auditory canal part, the area of interest including a portion of the conchal bowl part and a portion of the auditory canal part of the three-dimensional model, the area of interest of the three-dimensional model being selected so as to create an earpiece model that is substantially open in the conchal bowl portion and in the auditory canal part to ensure that the earpiece model is non-occlusive; and
   removing the portion of the three-dimensional occlusive computer model that does not include the area of interest, thereby obtaining an earpiece computer model for a hearing aid having a non-occluding conchal bowl part, a non-occluding canal area part, and a feature to enable cooperation with electronics located outside of the ear to aid hearing without occluding the conchal bowl and the auditory canal.

17. A system for producing a non-occluding earpiece for a hearing aid, said system comprising:
   a nontransitory computer readable memory having one or more computer instructions stored thereon, and
   a computer controllable prototyping machine, said prototyping machine being connected to the system to form an earpiece for a hearing aid from the non-occluding earpiece model generated by the system, and
   said instructions comprising instructions for conducting the steps of:

obtaining a scan of a conchal bowl in an outer ear and an auditory canal adjacent to the conchal bowl or of an impression of the conchal bowl in the outer ear and the auditory canal;

creating a three-dimensional occlusive computer model of at least a part of the conchal bowl and at least a part of the auditory canal from the scan, said three-dimensional occlusive computer model substantially conforming to a shape of the part of the conchal bowl or the part of the auditory canal or both, said model further including a feature to enable cooperation with electronics located outside of the ear to aid hearing without occluding the conchal bowl and the auditory canal;

selecting an area of interest of the three-dimensional model resulting in an earpiece model having a non-occluding conchal bowl part and a non-occluding auditory canal part, the area of interest including a portion of the conchal bowl part and a portion of the auditory canal part of the three-dimensional model, the area of interest of the three-dimensional model being selected so as to create an earpiece model that is substantially open in the conchal bowl portion and in the auditory canal part to ensure that the earpiece model is non-occlusive; and removing the portion of the three-dimensional occlusive computer model that does not include the area of interest, thereby obtaining an earpiece computer model for a hearing aid having a non-occluding conchal bowl part, a non-occluding canal area part, and a feature to enable cooperation with electronics located outside of the ear to aid hearing without occluding the conchal bowl and the auditory canal.

18. The system according to claim 17, wherein the prototyping machine is capable of performing 3D milling and/or stereo lithography/SLA and/or solid ground curing and/or selective laser sintering and/or direct earpiece production casting and/or 3D-printing and/or topographic earpiece fabrication and/or fused deposition modeling and/or inkjet modeling and/or laminated object manufacturing and/or nano-printing.

* * * * *